United States Patent [19]

Smith et al.

[11] 4,355,997
[45] Oct. 26, 1982

[54] METHOD FOR MEASURING THE LEVEL OF HYDROGEN SULFIDE IN GEOTHERMAL STEAM

[75] Inventors: Robert F. Smith, Long Beach; Dwight E. Walters, Cobb, both of Calif.

[73] Assignee: R. F. Smith Corp., Lakewood, Calif.

[21] Appl. No.: 273,951

[22] Filed: Jun. 15, 1981

Related U.S. Application Data

[63] Continuation-in-part of Ser. No. 80,684, Oct. 1, 1979, abandoned.

[51] Int. Cl.³ .................... G01N 33/24; G01N 33/18
[52] U.S. Cl. ................... 23/230 EP; 23/230 A; 23/230 R
[58] Field of Search .......... 23/230 EP, 232 R, 230 A

[56] References Cited

U.S. PATENT DOCUMENTS

| 2,341,169 | 2/1944 | Wilson et al. | |
| 2,923,151 | 2/1960 | Engle et al. | |
| 3,300,282 | 1/1967 | Risk et al. | 23/232 R |
| 3,422,674 | 1/1969 | Schroeter | |
| 3,462,751 | 8/1969 | Horeth et al. | |
| 3,529,937 | 9/1970 | Ihari et al. | 23/230 PC X |
| 3,838,972 | 10/1974 | Richards et al. | 23/232 R |
| 4,151,260 | 4/1979 | Woertz | |

Primary Examiner—Barry S. Richman
Attorney, Agent, or Firm—Christie, Parker & Hale

[57] ABSTRACT

A gaseous stream of steam is analyzed for hydrogen sulfide by keeping the gas stream above its dew point while withdrawing a representative sample, mixing the sample with a gas having a dew point lower than that of the gaseous stream to form a mixture with a dew point below that of the gaseous steam, and analyzing the mixture at a temperature above its dew point for hydrogen sulfide.

8 Claims, 6 Drawing Figures

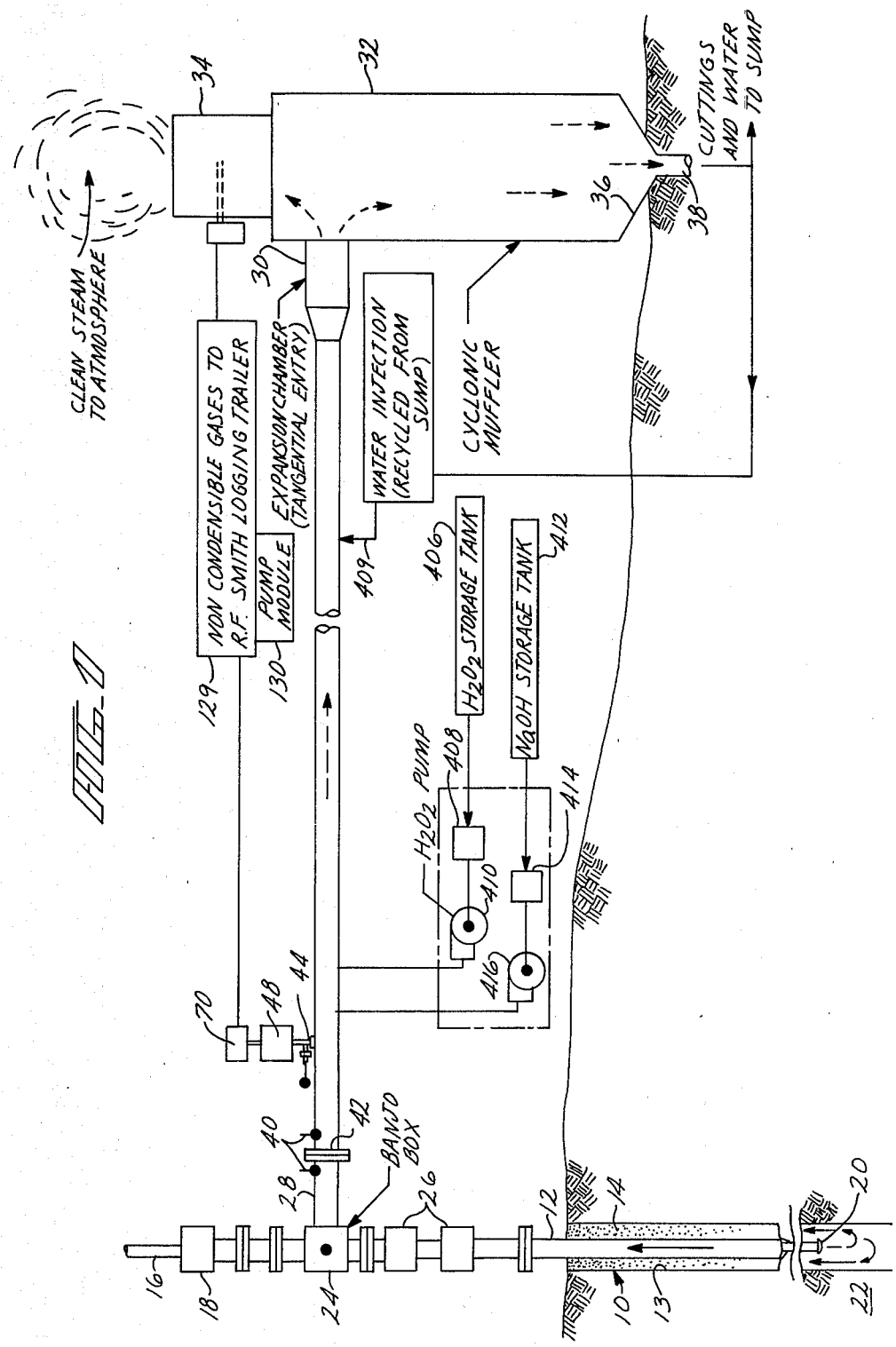

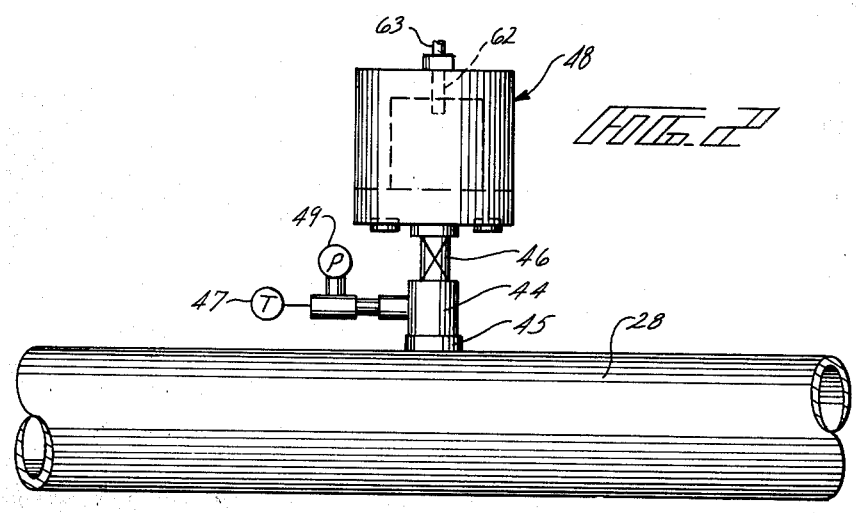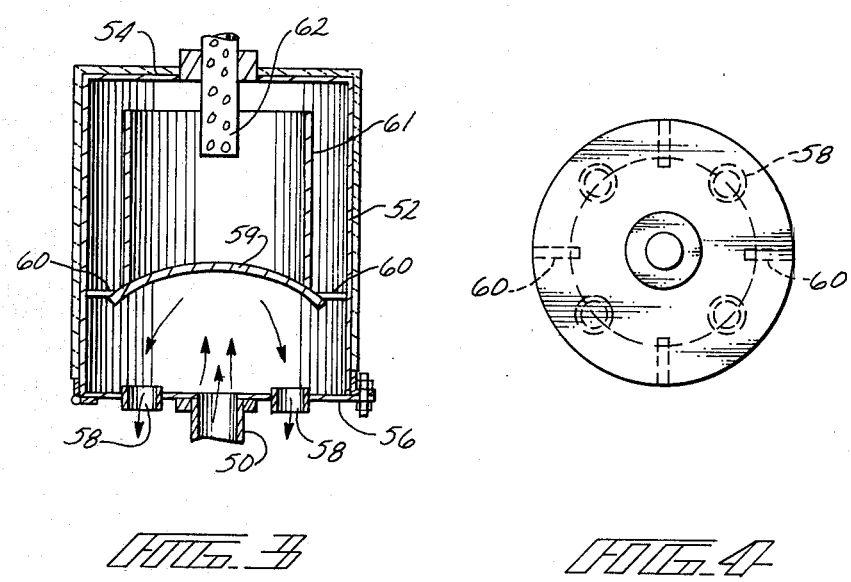

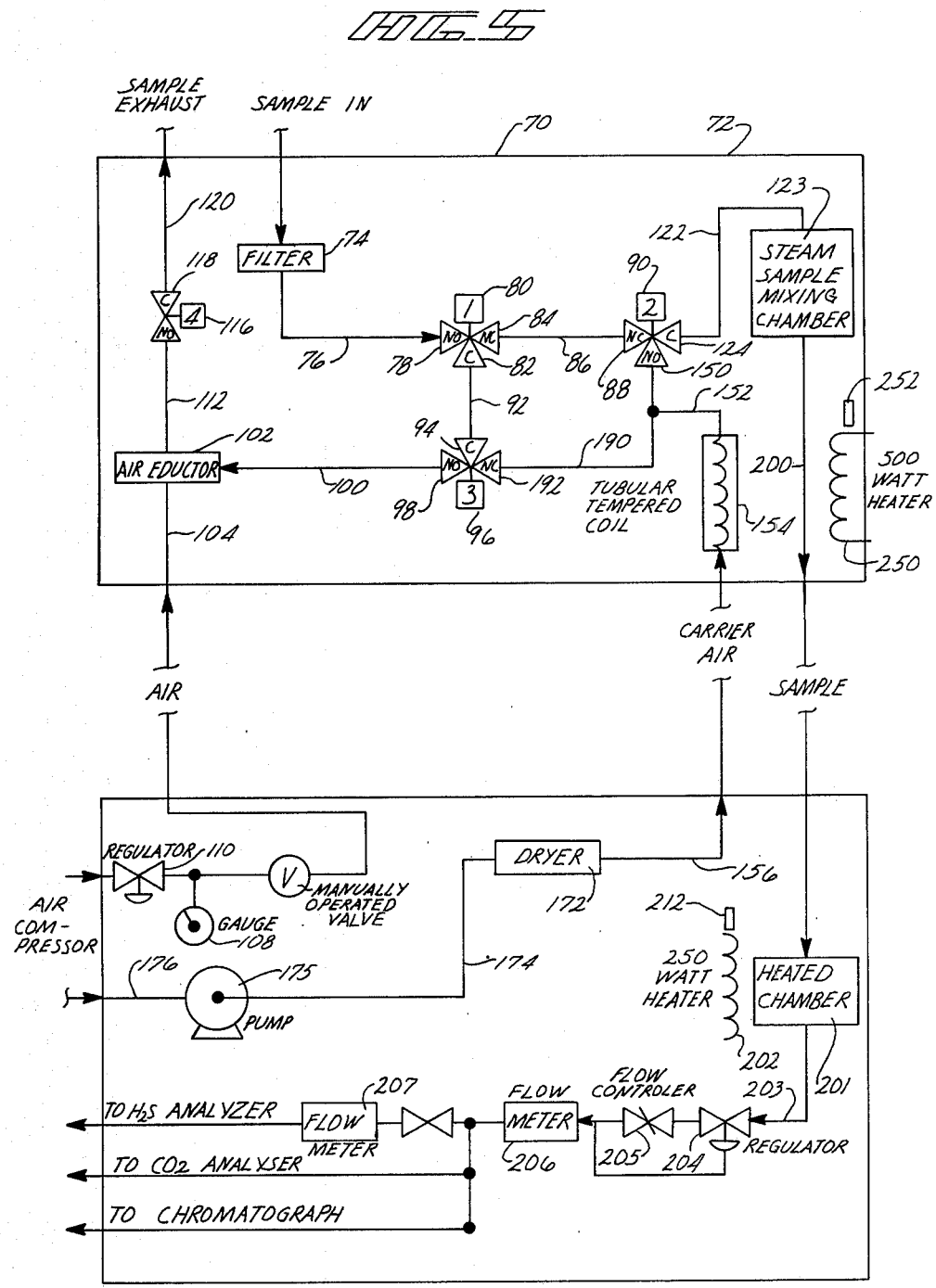

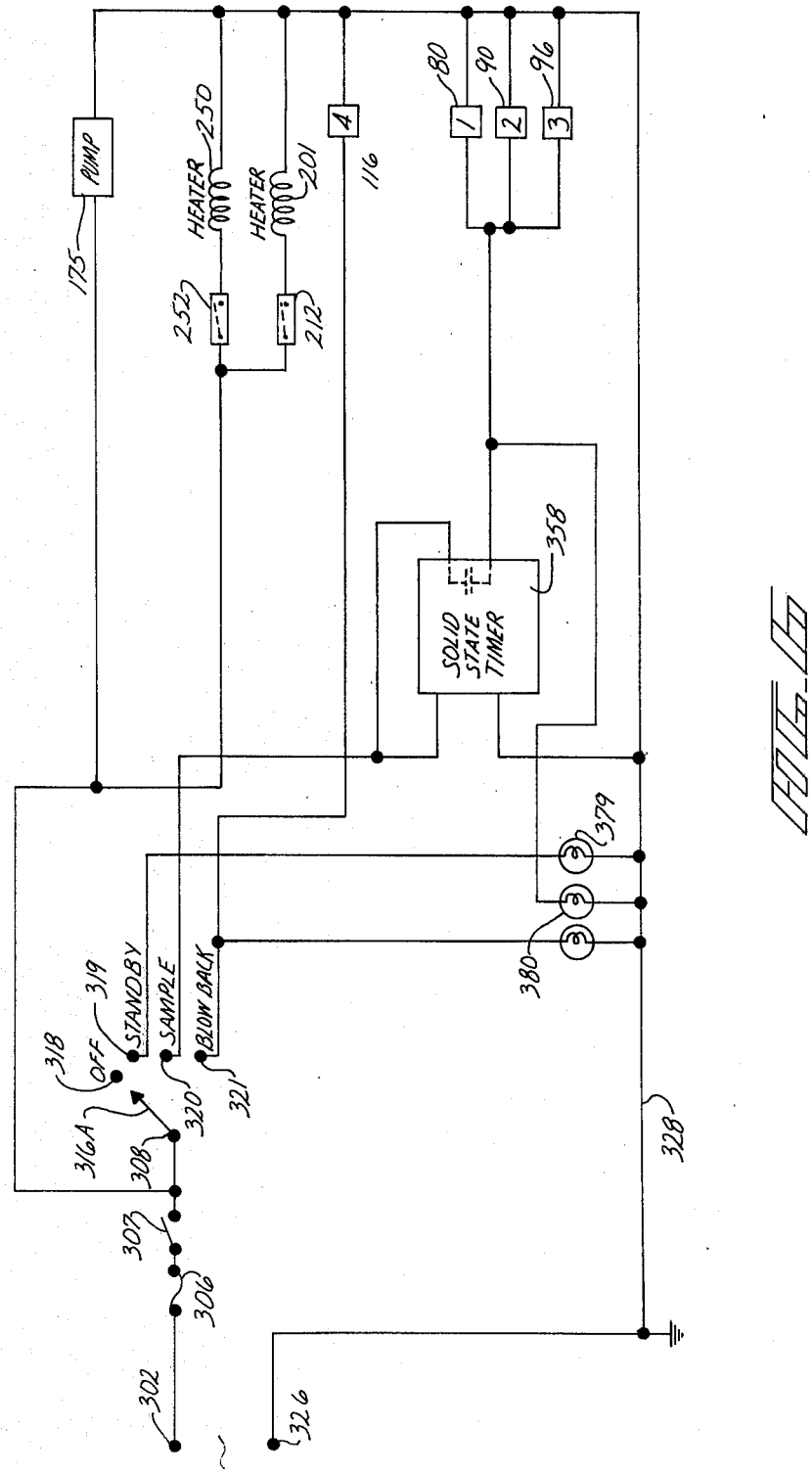

METHOD FOR MEASURING THE LEVEL OF HYDROGEN SULFIDE IN GEOTHERMAL STEAM

This application is a continuation-in-part of Ser. No. 80,684, filed Oct. 1, 1979 and now abandoned.

BACKGROUND OF THE INVENTION

This invention relates to the analysis of a gas stream which includes steam, such as that released during the drilling of a geothermal well, or from a steam power plant.

Geothermal energy is recovered by producing steam or hot water from underground reservoirs. The hot fluids are normally recovered by drilling a well sufficiently deep to penetrate the fluid-bearing portion of the reservoir. During the drilling operations, conventional drilling fluids are used to carry cuttings from the well bore. Ordinarily, the upper portion of the well is drilled with conventional drilling mud until the well nears the fluid-bearing portion of the reservoir. Thereafter, the well is drilled with compressed air as the drilling fluid to avoid plugging the formation from which steam or hot water is to be produced. Ideally, the producing formation is penetrated by the well under controlled blowout conditions, i.e., the pressure in the well bore is kept slightly below that of the fluids in the reservoir, so that net flow of fluids is from the reservoir into the well bore. Thus, the injected air and the fluids produced from the reservoir carry the formation cuttings to the surface. As the fluids approach the surface, reduced pressure usually results in the hot liquid water flashing to steam, if it was not already in that form. The steam, formation cuttings, and returning air are usually passed through a separator which removes the particulate matter from the stream of air and steam. Thereafter, the air and steam are discharged to the atmosphere.

Geothermal steam usually contains hydrogen sulfide gas, which is an odorous pollutant. Consequently, the emission of untreated geothermal steam to the atmosphere is undesirable, and is usually limited by environmental regulations.

Initially, regulatory agencies attempted to control geothermal emission of hydrogen sulfide by establishing emission for an entire geothermal field. Because of the variability of hydrogen sulfide emissions from individual wells, and because of the relatively large number of operators involved in geothermal exploration and production, the control of emission by geothermal field proved impractical. Accordingly, individual wells are now monitored for hydrogen sulfide during drilling and testing, and abatement procedures are put into effect as required. For example, some new regulations require that the air pollution not exceed 2.5 kilograms of hydrogen sulfide per hour per well.

Although geothermal well drilling is only a minor, transitory source of hydrgeon sulfide emission, the hourly emission standards can be exceeded for short periods of time. Emissions from steam power plants are also a potential source of hydrogen sulfide, if the steam used by the plants has not been properly treated. Such emissions can be controlled by down-hole injections of ammonia or by blooie line injection of aqueous hydrogen peroxide and sodium hydroxide solutions into the stream of steam and hydrogen sulfide, as disclosed in U.S. Pat. No. 4,151,260, issued Apr. 24, 1979, to Woertz. It is important, therefore, to monitor accurately the hydrogen sulfide concentration in gaseous streams from wells and power plants to assure compliance with emission regulations, and to determine the optimum hydrogen sulfide abatement procedures.

In the past, hydrogen sulfide produced from a geothermal well has been determined by removing a bulk sample from the stream of gas flowing from the well, removing solids, condensing the steam in the sample, and thereafter analyzing the residual gas. We have found that the condensation of steam introduces serious errors into the analysis for hydrogen sulfide. First, hydrogen sulfide is absorbed by the condensed steam, which causes a reduction in the observed concentration of hydrogen sulfide. An offsetting problem is that concentration of hydrogen sulfide observed in the vapor phase remaining after condensation of the steam depends upon the solubility and partial pressure of hydrogen sulfide in the condensate at various temperatures along the sample line. This could cause excessively high or low readings at the analyzer. For example, the lowering of the condensate temperature reduces the amount of hydrogen sulfide in the vapor phase at equilibrium conditions. A change of 10° C. can change the observed hydrogen sulfide concentration by 40% or more. Such changes can occur due to variable weather or operating conditions and, therefore, introduce serious error in the analysis. Moreover, changes in the percent of noncondensibles, the flow rate of the drilling air, and the pH of the condensate affect the observed concentration of hydrogen sulfide.

This invention provides an apparatus and method for taking and analyzing a representative sample of a gas stream of steam and other gases free of the errors referred to above.

SUMMARY OF THE INVENTION

In terms of method for analyzing a gaseous stream of steam and hydrogen sulfide produced from a geothermal formation, the invention includes the steps of flowing the gaseous stream through a conduit and into the atmosphere. A sample of the gaseous stream is removed from the conduit at a temperature above its dew point. A gas with a dew point lower than that of the gaseous stream is added to the sample to form a mixture with a dew point below that of the stream. Thereafter, the mixture is analyzed at a temperature above its dew point for hydrogen sulfide.

In the preferred method, the gas added to the stream is ambient air which has been dried and heated to prevent condensation of any significant amount of steam during the mixing step.

The preferred method also includes the step of separating solid particles from the sample, while keeping the sample at a temperature above its dew point to prevent formation of liquid water, which would absorb some hydrogen sulfide from the vapor phase of the sample.

In terms of apparatus for analyzing a gaseous stream of water vapor and a first gas, the apparatus includes a thermally-insulated housing and means for maintaining the temperature in the housing above the dew point of the gaseous stream. Means are also provided for flowing the gaseous stream through a sampling conduit in the housing. Means are also provided for flowing a second gas through a transport conduit in the housing. The transport conduit has an outlet connected to a gas analyzer, and means are provided for transferring the gaseous stream in the sampling conduit into the second gas as it flows through the transport conduit.

The preferred form of the apparatus includes a gas-solid separator maintained at a temperature above the dew point of the gaseous stream and connected between the gas stream and the inlet of the sampling conduit. A filter is also included between the gas-solids separator and the inlet of the sample conduit, and means are provided for backflushing the filter.

BRIEF DESCRIPTION OF THE DRAWINGS

FIG. 1 is a schematic drawing of a well drilling operation in which the method and apparatus of this invention may be used;

FIG. 2 is an elevation of a portion of the apparatus shown in FIG. 1 enlarged to show the preferred embodiment of the gas-solids separator in vertical cross-section;

FIG. 3 is a view taken on line 3—3 of FIG. 2;

FIG. 4 is a view taken on line 4—4 of FIG. 3;

FIG. 5 is a schematic diagram of the flow conduits and control valves for processing the sample in accordance with this invention; and FIG. 6 is a schematic circuit diagram of the electrical controls for the valves and pumps shown in FIG. 5.

DESCRIPTION OF THE PREFERRED EMBODIMENT

Referring to FIG. 1, a well 10 includes a casing 12 secured in the upper end of a well bore 13 by cement 14. A drill string 16 extends down through a rotating seal 18 on the upper end of the casing. The drill string extends downwardly from the lower end (not shown) of the casing, and carries a drill bit 20. The drill string is rotated by a conventional rotary table (not shown) mounted on a conventional drilling rig (not shown).

As shown in FIG. 1, the drill bit penetrates a formation 22, which contains a reservoir of high-pressure geothermal steam. Accordingly, the drilling fluid used is air supplied from a compressor (not shown) through a conventional rotary swivel (not shown) on the upper end of the drill string. The pressure in the well bore in the vicinity of the drill bit is maintained below that of the adjacent formation pressure so that drilling air from the compressor, solid drill cuttings, and steam from the formation flow up through the annular space between the casing and drill bit to a "banjo box" 24 installed in the casing above a pair of blowout preventers 26 and below the rotating seal 18.

A horizontal blooie line 28, connected to the banjo box, carries a gaseous stream of steam, drill cuttings, injected air, and formation gases to an expansion chamber 30, which is connected to a conventional cyclonic muffler separator 32 having an outlet 34 at its upper end to discharge steam to the atmosphere, and a downwardly and inwardly tapering bottom 36 connected to a discharge line 38 for the removal of drill cuttings and water to a sump (not shown).

Orifice taps 40 on opposite sides of an orifice plate 42 in the blooie line permit the measurement of gas flow from the well.

A bulk sampling line 44 opens into the blooie line through a connecting collar 45 secured to the outside of the blooie line. Sampling line 44 is sealed through the blooie line wall and connected by a ball valve 46 to the bottom end of a steam separator 48. A T-connection in the line 44 directs gas to a thermocouple 47 and pressure measuring transducer 49.

The steam separator 48 includes a hollow cylindrical body 52 closed at its upper end by a top 54 and at its lower end by a flat plate 56 secured to the blooie line through the sampling line 44. As shown best in FIGS. 2-4, the plate 56 includes a central collar that connects to the ball valve 46 through a nipple 50. Openings 58 through the plate 56 permit the escape of solids and some gas flowing through the separator.

The separator includes a concave solid baffle plate 59 supported by brackets 60. On top of the baffle plater is a container 61 open at the top. The top edge of the container is spaced below the top 54 of the separator. A perforated strainer tube 62 extends down into the container 61, providing a gas outlet at the top of the separator which connects to an output line 64. Most of the incoming stream impinges on the baffle 59 and is directed out the openings 58 in the bottom of the separator together with most of the entrained solids. A sample of the gas passes up over the top of the container and out the perforated tube 62. Any solids still present are caught in the container or by the tube.

A sample of the gas stream then flows from the separator through an outlet 62 and the line 64 after passing through the separator. Ordinarily, all of the solids are removed from the sample, because most of the bulk sample passes substantially straight through the separator. For example, only a minor portion, say, less than 2%, of the bulk sample flows from the separator output line 64. Thus, most of the bulk sample flows at a relatively high speed out the openings 58 in the plate 56 at the bottom of the separator. The sample which leaves through line 64 flows at a relatively slow rate so that the momentum of the solids flowing down through the separator is sufficiently high to keep all, or substantially all, of them from making the change of direction necessary to leave through line 64 in the upper portion of the separator. The sample from the steam separator and strainer flows through the line 64 to a steam sampler module 70 shown in detail in FIG. 5.

The steam sampler module includes a thermally-insulated housing 72. Sample from insulated line 64 flows through a conventional dry filter 74 in the housing and through a line 76 to a normally open port 78 of a first three-way solenoid-operated valve 80, which includes a common port 82 that is always open. A normally closed port 84 of the first valve 80 is connected by a line 86 to a normally closed port 88 of a second three-way solenoid-operated valve 90.

A sample loop line 92 connects the common port 82 of the first valve 80 to a common port 94 of a third three-way solenoid-operated valve 96. The common port 94 of the third valve 96 is always open as are all the respective common ports of the solenoid-operated valves described below. A normally open port 98 of the third valve is connected by line 100 to the suction inlet of an eductor 102, which is supplied eductor air through a line 104 from an air compressor (not shown). A first gauge 108 on line 104 measures air pressure in the line, and a regulator 110 in the supply line 104 controls the amount of eductor air flowing through the eductor. Air and educed sample flows from the eductor through a line 112 into a normally open port 114 of a two-way solenoid-operated valve 116. The mixture of educed sample and eductor air flows out of the fourth solenoid-operated valve 116 through a common port 118, which is always open, and which is connected through a vent line 120 to the atmosphere outside the insulated housing of the stream sampler module. Thus, when the first four solenoid-operated valves are not energized, sample is drawn continuously through the sample loop line and the eductor to be vented to the atmosphere.

A normally open port 150 of the second solenoid-operated valve 90 is connected by a line 152 to the outlet of a tubular tempering coil 154, the inlet of which is connected through a line 156 to a dry air source. The source includes a pump 175 and a dryer 172 which is full of a suitable dessicant, such as calcium sulfate. A line 174 connects the inlet of the dryer to the outlet of the pump 175. Ambient air is drawn into the pump inlet through a line 176. Five liters per minute is usually satisfactory.

A sample carrier line 122 connects a common port 124 of the second solenoid-operated valve 90 to a baffled steam sample mixing chamber 123. A sample carrier line 200 connects the output of the mixing chamber to the control module 168 and may be made of any of the well-known plastics used in steam sterilizers which can withstand temperatures greater than 212° F. The line 200 is sufficiently insulated to prevent condensation of moisture in it and may even be heated when the environment requires it.

Returning to the steam sampler module 70, a lateral line 190 connects the outlet end of the tubular tempering coil 154 to a normally closed port 192 of the third solenoid-operated valve 96. An electrical heating element 250 in the steam sampler module housing 72 is controlled by a thermostat switch 252 in the housing, as described in detail below. The thermostat maintains the temperature in the sample module at approximately 250° F.

The carrier line 200 connects the mixing chamber 123 in the steam sampler module to the inlet of a heater chamber 201 in the control module 168 which maintains the sample above the dew point of the steam and air mixture. The chamber 201 is electrically heated by a resistance heater 202. A thermostat 212 maintains the temperature inside the control module at approximately 125° F. which is high enough to prevent precipitation yet low enough to permit operation of the electronic circuits associated with the flow meters and analyzers. The output line 203 is connected to a regulator 204 and a flow controller 205 before passing through a flow meter 206. The outlet of the flow meter is connected to a hydrogen sulfide analyzer through another flow meter 207, to a $CO_2$ analyzer, and to a chromatograph. The analyzers may be of any suitable conventional type.

Referring to FIG. 6, which is a schematic diagram of circuits and equipment in the control and steam sampler modules, one terminal 302 of an a.c. power source is connected through a fuse 306 and ON-OFF switch 307 to the common terminal 308 of a four-contact rotary control switch 315. Movable arm 316 can be turned to connect terminal 302 of the power source to any one of the contacts 318, 319, 320, and 321. A second terminal 326 of the power source is connected to a common grounded conductor 328, which completes the circuits, as described below. One side of the thermostat switches 212 and 252 are connected to the main power switch 307 so that the heaters 201 and 250 are turned on when the main power switch is closed.

First contact 318 is open so that the switch 315 is in the OFF position when the movable arm engages that contact. When the control switch arm engages the second contact 319, a STANDBY light 379 is on. In STANDBY, the pump 175 continues to provide air through the deenergized valve 90 to the analyzers while the sample gas is directed by the deenergized valves 80 and 96 through the eductor to the sample exhaust.

When the switch 315 is moved to the third contact, the SAMPLE position, input power is connected to a solid state timer 358. The timer is adjustable to control the period and duty cycle of a flip-flop that operates a relay within the timer. The timer relay opens and closes a circuit between the power source and the three solenoid valves 80, 90 and 96 in the stream sample module 70. The valves are turned on by the timer 358 for a controlled interval and then turned off for a controlled interval. Power is supplied also to a second light 380 in parallel with the solenoid valves, which indicates that the system is operating to dilute the sample passing through the sample conduit loop by a ratio controlled by the setting of the timer, e.g., 100 volumes of air to 1 volume of sample, as explained in detail below.

When the control switch arm engages the fourth contact, the BLOWBACK position, the fourth contact supplies power to the fourth solenoid valve 116 to shut off flow to the sample exhaust. This causes the air from the compressor to be forced out of the vacuum side of the eductor 102 in a reverse flow direction, through the normally open side of the deenergized valves 80 and 96, and through the filter 74 and sample input line. Thus air is used to back flush the sample filter 74 and the steam separator 48. A light 381 indicates when the blowback operation is on.

In using the equipment just described, it is connected to a well, as shown in FIGS. 1-6. A typical geothermal well may produce about 150,000 pounds of steam per hour with a hydrogen sulfide concentration of about 220 ppm. The gas stream from the well flows through the banjo box and the blooie line. The orifice plate in the blooie line can be used to determine exact flow rate from the well. The mixture of drill cuttings, steam, hydrogen sulfide, and other gases, such as carbon dioxide, hydrocarbons, and the like, flow from the blooie line, into the expansion chamber, and through the cyclonic muffler. Clean steam is vented from the muffler to the atmosphere through outlet 34. Condensed steam and drill cuttings discharge from the bottom of the muffler through line 38 into a sump. Water is injected through a line 404 into the blooie line just upstream of the expansion chamber to wet the solid particles and facilitate their removal from the gas stream. The injected water also reduces noise level from the cyclonic separator. Conveniently, the water comes from the sump.

A solution of hydrogen peroxide is injected from a source 406 through flow meter 408 and a chemical pump 410 into the blooie line. A solution of sodium hydroxide is injected from a source 412, through a flow meter 414, and a chemical injection pump 416 into the blooie line. The hydrogen peroxide and sodium hydroxide are injected downstream of the sample bulk sampling line 44, but well upstream of the cyclonic separator, to permit hydrogen sulfide abatement, as described in U.S. Pat. No. 4,151,260. A gaseous stream of bulk sample from the mainstream flows from the blooie line, through the line 44 into the separator 48. Steam and solid particles pass almost directly through the separator and out the holes 58 in the plate on the bottom of the separator. The bulk sample flows from the separator through line 64. Since the separator 48 is thermally insulated, and even heated if necessary, there is no condensation of steam in the withdrawn bulk sample. The selected sample passes through the dry filter 74, which removes particulates down to 0.6 micron.

With the control switch set to the SAMPLE position, the pump 175 in the pump module is run to deliver a supply of dry air through the dryer 172 to the inlet end of the baffled chamber 123 in the steam sampler module, which is kept at a temperature about 250° F. by the heater 250. The temperature of the valves and lines in the steam sampler module are also kept above the dew point of the gaseous stream from the well by the heater 250. Compressed ambient air from the eductor air line 104 to the eductor 102 causes sample gas to be drawn through the first three-way valve 80, the sample conduit loop 92, the third three-way valve 96, and into the inlet leg 100 of the eductor. The sample is exhausted through the fourth valve 116. The sample conduit loop has a relatively small total volume, say 5 cc., so that it is quickly filled with filtered sample from the gaseous stream produced by the well. The timer 358 causes the respective solenoids for the first, second, and third three-way valves to close every 10 seconds for a period of approximately 2 seconds, so that the normally open ports of those valves are closed, and the normally closed ports open. During this interval, heated, dry air from the tempering coil 154 flows through line 190, the third three-way valve 96, the sample conduit loop 92, the first three-way valve 80, the second three-way valve 90, and line 122 to the baffled mixing chamber 201 in the control module. The pump 175 and flow controller 205 in the control module combine to supply a known volume of air, say, 3,000 cc. per minute. Since the timer 358 cycles every ten seconds, the carrier air from the tempering coil picks up 5 cc. of sample six times each minute. Accordingly, the mixture which enters the mixing chamber contains on the average 30 cc. of sample for each 2,970 cc. of carrier air, resulting in a sample dilution of 100:1 by volume. The sample gas and dry air are mixed completely by the chambers 123 and 201 so that a continuous flow of accurately diluted (100:1) sample gas is delivered to the analyzers at a constant flow rate.

The air coming out of the dryer has a dew point of about −100° F. Since the air is heated as it flows through the mixing chamber in the steam sampler module, the sample is not exposed to any condition under which steam can condense, and the mixture of sample and carrier air has a dew point well below the original dew point of the gaseous stream produced by the well. Accordingly, the mixture of carrier air and sample can be allowed to cool to a workable temperature (e.g., 90° F.–125° F.) before it enters the analyzers and analyzed without any significant condensation of steam from the mixture. This permits analysis to take place at ambient temperature, except perhaps under the most extreme weather conditions, in which case, the lines from the steam sampler module to the control module can be insulated, or even heated, as required, to keep the mixture above its dew point.

The operator using the control module analyzes the gas for its various components by any of the well-known methods by selectively passing the gas through the various analytical equipment.

If the sample is to be diluted 20:1, for example, timer 358 may be reset to cycle every two seconds and the ON time set about 1.0 second. This mode of operation is identical with that just described, except that 5 cc. of sample are injected into the carrier stream of air thirty times per minute, giving a dilution ratio of 20:1.

A second steam sampler 430 (identical with sampler 70 described above) in the outlet of the cyclonic muffler can draw a sample exactly as described for the first sampler, so that the effectiveness of the treatment of the gaseous stream from the well may be verified. Moreover, the analysis of the gaseous stream from the well, both before and after treatment, can be used to control the injection of chemicals for optimum abatement of hydrogen sulfide emission.

If the operator suspects that the filter is plugged and wants to backwash it, he does so by setting the control switch to the BLOWBACK positioning so that power is supplied to the solenoid of the two-way valve 116 in the steam sampler module. This closes the valve and causes air to flow through line 104 and out the eductor inlet line 100, through the third three-way valve 96, the sample conduit loop 92, the first three-way valve 80, and through the filter 74, because the normally open port of the fourth three-way valve 116 is now closed.

When it is desired to flush the analytical equipment with clean, dry air, the control switch is turned to the STANDBY position. Under these conditions, clean, dry air from pump 175 flows through the second three-way valve 90 and out to the control module. At the same time, the sample conduit loop 92 is flushed with sample gas continuously and without injection of the sample into the carrier stream. Compressed air supplied to the eductor pulls sample through the sample conduit loop continuously. Clean, dry air also flows continuously through the chambers 123 and 201, but bypasses the sample conduit loop.

From the foregoing description, it will be apparent that this invention permits a gaseous stream containing a large amount of steam to be sampled and analyzed at temperatures substantially below the dew point of the gaseous stream without adversely affecting the accuracy of the analysis due to condensation of steam in the sample. Moreover, the method and apparatus can be used to analyze any gaseous stream, whether it is at the well site, from a steam power plant, or any other source. The accurate sampling and analysis system made possible by this invention also permits the output of the hydrogen sulfide analyzer to be used to control the rate at which hydrogen peroxide and sodium hydroxide are injected into the blooie line to achieve adequate abatement without waste of chemicals. The pressure drop across the orifice plate, as measured by the orifice taps, indicates the flow rate of the gaseous stream through the blooie line. This information, taken in conjunction with the hydrogen sulfide concentration in the gaseous streams, permits the automatic control of the injection of hydrogen peroxide and sodium hydroxide to obtain the desired hydrogen sulfide abatement without wasteful use of an excessive amount of those chemicals.

What is claimed is:

1. A method for continuously measuring the amount of hydrogen sulfide present in a continuous gaseous stream of steam containing hydrogen sulfide as a pollutant produced from a geothermal formation, the method comprising the steps of:

keeping the gaseous stream above its dew point;
mixing the gaseous stream of steam with a continuous stream of dilution gas in a fixed predetermined ratio by volume to lower the dew point of the gas mixture, the dilution gas being substantially free of said pollutant, keeping the temperature of the mixed gas stream at a temperature above the lowered dew point of the mixture but below the dew point of the gaseous stream from the geothermal formation, and continuously measuring the level of hydrogen sulfide in the mixed gas stream at the reduced temperature.

2. A method according to claim 1 which includes the step of adding the dilution gas at a temperature which prevents condensation of steam during mixing.

3. A method according to claim 1 in which the gaseous stream includes solid particles, and which includes the step of removing solid particles from the gaseous stream before adding the dilution gas to form the mixture.

4. A method according to claim 1 in which the dilution gas is air.

5. A method according to claim 4 which includes the step of dehumidifying the air before adding it to the gaseous stream.

6. A method according to claim 4 which includes the step of heating the air above ambient temperature before mixing.

7. A method of continuously measuring the proportion of sulfur pollutants in a stream of geothermal steam, comprising the steps of:

removing a fixed volume sample from the stream at predetermined equal time intervals, maintaining the stream and samples at a temperature above the dew point of the geothermal steam, adding each of the samples as they are removed from the stream to a continuous stream of a heated dilution gas having a very low dew point, mixing each of the samples of geothermal steam with the dilution gas to reduce the dew point of the geothermal steam, maintaining the flow rate of the dilution gas at a predetermined constant level, whereby the proportion of sampled gas and dilution gas in the mixed gas stream is substantially constant, reducing the temperature of the mixed gas stream to a temperature above the dew point of the mixed gas but substantially below the dew point of the stream of geothermal steam, and measuring the concentration of sulfur pollutant in the mixed gas stream at the reduced temperature.

8. A method of claim 7 further including the step of: adjusting said time intervals at which the samples are removed to control the ratio of geothermal steam and dilution gas in the mixed gas stream.

* * * * *